US012797512B2

(12) United States Patent
Huri et al.

(10) Patent No.: US 12,797,512 B2
(45) Date of Patent: Nov. 17, 2026

(54) HYBRID, ARTIFICIAL BONE TISSUE IMPLANT ABSORBING MECHANICAL VIBRATIONS, WHOSE ARCHITECTURAL STRUCTURE IMITATES TRABECULAR BONE, ALLOWING THE SATURATION OF BONE MARROW, BLOOD, AND NUTRIENTS, SUPPORTING AUTOLOGICAL REGENERATION, WHICH CAN BE USED WITH TITANIUM STRUCTURES

(71) Applicant: BLOOCELL SAGLIK TEKNOLOJILERI SANAYI VE TICARET LIMITED SIRKETI, Sakarya (TR)

(72) Inventors: Gazi Huri, Ankara (TR); Oktay Topaloglu, Sakarya (TR); Mustafa Cüneyt Cikman, Kocaeli (TR)

(73) Assignee: BLOOCELL SAGLIK TEKNOLOJILERI SANAYI VE TICARET LIMITED SIRKETI, Sakarya (TR)

( * ) Notice: Subject to any disclaimer, the term of this patent is extended or adjusted under 35 U.S.C. 154(b) by 529 days.

(21) Appl. No.: 18/286,764

(22) PCT Filed: Dec. 26, 2021

(86) PCT No.: PCT/TR2021/051516
§ 371 (c)(1),
(2) Date: Oct. 13, 2023

(87) PCT Pub. No.: WO2022/220766
PCT Pub. Date: Oct. 20, 2022

(65) Prior Publication Data
US 2024/0197958 A1 Jun. 20, 2024

(51) Int. Cl.
*A61F 2/28* (2006.01)
*A61L 27/34* (2006.01)
(Continued)

(52) U.S. Cl.
CPC ............... *A61L 27/34* (2013.01); *A61L 27/46* (2013.01); *A61L 27/52* (2013.01); *A61L 27/56* (2013.01);
(Continued)

(58) Field of Classification Search
CPC ........... A61L 27/34; A61L 27/46; A61L 27/52
See application file for complete search history.

(56) References Cited

U.S. PATENT DOCUMENTS

2008/0147197 A1* 6/2008 McKay .................. A61L 27/54 206/570
2019/0009004 A1* 1/2019 Liu ......................... A61L 27/12
2020/0397542 A1* 12/2020 Andersen ............... A61C 13/00

FOREIGN PATENT DOCUMENTS

CN 103990182 A 8/2014
CN 107854726 A 3/2018
(Continued)

*Primary Examiner* — Dah-Wei D. Yuan
*Assistant Examiner* — Kristen A Dagenais
(74) *Attorney, Agent, or Firm* — Bayramoglu Law Offices LLC

(57) ABSTRACT

A polymer scaffold structure is created as a result of the proportional combination of β-Tricalcium Phosphate (β-TCP) that will increase the 3D and osteoconductive effect allowing/supporting cell infiltration by using extrusion deposition, in other words, added manufacturing process, and with physiological buffered HA solution with the Deep Coating Method and by increasing the transmission rate of growth factors as a result of coating and expanding their areas with the biological tissue implant, which allows its use with titanium mesh plates or contoured structures.

20 Claims, 2 Drawing Sheets

DETAIL D

(51) Int. Cl.

*A61L 27/46* (2006.01)
*A61L 27/52* (2006.01)
*A61L 27/56* (2006.01)
*A61L 27/58* (2006.01)
*B33Y 80/00* (2015.01)
*C08L 5/08* (2006.01)

(52) U.S. Cl.

CPC ............... *A61L 27/58* (2013.01); *B33Y 80/00* (2014.12); *C08L 5/08* (2013.01); *A61L 2430/02* (2013.01); *A61L 2430/06* (2013.01)

(56) References Cited

FOREIGN PATENT DOCUMENTS

| | | | |
|---|---|---|---|
| CN | 111973811 | A | 11/2020 |
| CN | 112590203 | A | 4/2021 |
| TR | 201618844 | | 4/2017 |
| TR | 201811205 | | 11/2018 |
| TR | 201912510 | | 9/2019 |
| WO | 2018078130 | A1 | 5/2018 |

* cited by examiner

DETAIL C

SECTION C-C

HYBRID, ARTIFICIAL BONE TISSUE IMPLANT ABSORBING MECHANICAL VIBRATIONS, WHOSE ARCHITECTURAL STRUCTURE IMITATES TRABECULAR BONE, ALLOWING THE SATURATION OF BONE MARROW, BLOOD, AND NUTRIENTS, SUPPORTING AUTOLOGICAL REGENERATION, WHICH CAN BE USED WITH TITANIUM STRUCTURES

CROSS REFERENCE TO THE RELATED APPLICATIONS

This application is the national phase entry of International Application No. PCT/TR2021/051516, filed on Dec. 26, 2021, which is based upon and claims priority to International Application No. PCT/2021/006756, filed on Apr. 17, 2021, the entire contents of which are incorporated herein by reference.

TECHNICAL FIELD

This invention is related to biological tissue implant that allows its use with titanium mesh plaque or contoured structures, by creating a scaffold structure (tissue scaffold) as a result of the proportional combination of 3D polymer that allows/supports cell infiltration and β-Tricalcium Phosphate (β-TCP), which will increase the osteoconductive effect, by using extrusion deposition, in other words, added manufacturing process, and the deep coting method and by increasing the transmission rate of the growth factors and expanding their area as a result of coating with physiological-buffer HA solution.

BACKGROUND

There are bioresorbable implants used in surgeries to repair various fractures such as foot fractures and to fill surgical defects. The bone marrow allows saturation with blood and nutrients with the developed architecture, thereby providing the patient's cells with the chemical signals needed for bone growth and remodeling. The meshwork or pores provide a rigid but flexible scaffold with adequate mechanical strength to support the growth of bone. As bone regeneration and remodeling takes place, it deteriorates. Long-term clinical trials showed that it provides significant bone regeneration because the materials are slowly absorbed by the body and replaced by autologous bone.

The tissue engineering field has advanced at a significant level in the last decade offering the potential to regenerate almost every tissue and organ of the human body. A typical tissue engineering strategy can be broken down into three components, which are the scaffold, the cells, and the biological factors. The scaffold serves as a template for tissue regeneration playing important roles in cell adhesion, proliferation, differentiation, and new tissue formation. The features expected from an ideal scaffold can be listed as follows, biocompatible and biodegradable structure with controllable degradation rates, decomposition products that will not cause inflammation and toxicity, a 3D and porous design to support cell adhesion, penetration, proliferation, and Extracellular Matrix (ECM (Extracellular matrix)) deposition, a network of interconnected pores to facilitate the passage of nutrients and waste, a suitable mechanical strength to support regeneration, and suitable surface chemistry and surface topography to promote cellular interactions and tissue development. Osteoconductivity is needed because of its porosity, and biodegradation, which are essential properties for scaffolds to be successful in bone tissue engineering applications, increase bone formation and angiogenesis and support osteoblast attachment and proliferation. Scaffolds can be produced from a variety of materials, including metals, ceramics, and polymers. Metallic alloys are used widely for dental and bone implants, and ceramics that have good osteoconductivity are used for bone tissue engineering. However, polymer materials are the dominant materials in the field of tissue engineering since metals are not biodegradable and cannot provide a matrix for cell growth and tissue formation. Ceramics also have limited biodegradability and cannot be processed as porous structures with their brittleness. Generally, polymer materials that are employed for scaffold production are immunologically advantageous as they are easy to process, biodegradable, and affect cell adhesion and function positively. For this reason, functionalized scaffolds can be produced that combine the advantage of both synthetic and natural polymeric materials by incorporating bioactive substances into synthetic polymers.

Polycaprolactone (PCL) is a fully biodegradable, thermoplastic polyester that has potential applications for bone and cartilage repair, and has been used successfully as a scaffold material in a variety of areas. PCL has thermal stability in the melted state with its positive features such as low glass transition temperature (60° C.), low melting temperature (60° C.), and high decomposition temperature (350° C.). For this reason, semicrystalline PCL reaches a rubbery state at physiological temperature, and this results in high toughness and superior mechanical features (e.g. high strength and elasticity depending on its molecular weight) [9]. PCL degrades very slowly when compared to other biopolymers used in the body, and is suitable for use in long-term load-bearing applications with its high hydrophobicity and crystallinity. Various studies are conducted to produce PCL biocomposites with both natural and synthetic polymers and copolymers. PCL scaffolds can be produced with various rapid prototyping techniques e.g. FDM, SLS, low temperature, and multi-nozzle added manufacturing in which it was observed that the cells began to grow by adhering to the PCL scaffolds, and the feasibility of the produced scaffolds was demonstrated in vitro and in vivo. PCL, which is a synthetic biodegradable aliphatic polyester, is relatively inexpensive compared to other biomaterials, and its ability to mold into different forms makes it different from other biomaterials employed in scaffold development. PCL is an FDA-approved polyester and is suitable for both load-bearing and non-load-bearing tissue engineering applications. For this reason, it is also suitable for surface changes, its features such as hydrophobicity and degradation can be changed greatly. Recent advances in tissue engineering have led to the development of a scaffold that has ideal features by using composites or mixtures. With its hydrophobic nature, which affects the cell attractant properties of PCL, it is used in many experiments for blending with natural polymers, functionalizing its surface by using short amino acid stretches and peptide sequences such as fibrin. Adhesion, proliferation, and differentiation of seeded cells are enhanced by improving their biocompatibility.

Hyaluronic Acid (HA) is a glycosaminoglycan in extracellular tissue in many parts of the body as an increasingly important material for the science of biomaterials and finds applications in a wide variety of fields from tissue culture scaffolds to cosmetic materials. Its physical and biochemical features in solution or hydrogel form make it extremely attractive for technologies related to body repair. Since HA is rich in carboxyl and hydroxyl groups, it can form a hydrogel under conditions such as chemical modification, cross-linking, or photo-crosslinking. The mechanical strength and physical and chemical features of materials depend on the degree of modification and crosslinking. The purpose of cross-linking HA is to convert it from solid-state to hydrogel state under suitable conditions and prolong its residence time in the human body. Also, the mechanical strength of the cross-linked HA is higher at significant levels when compared to non-crosslinked ones, and makes it more suitable for tissue engineering applications. Cross-linked HA shows relatively higher mechanical features compared to its linear state. For this reason, its use as a composite may combine the advantages of different materials.

The technique that is employed to produce PCL scaffolds depends on the type of scaffold required. Methods such as 3D printing, phase separation technique, and freeze-drying are used for porous scaffolds. However, techniques e.g. electrospinning are also used to produce fibrous scaffolds. Features such as pore structure, pore size, hardness, and permeability require precise process control. For this reason, 3D printing technology can overcome many of the limitations of traditional manufacturing techniques offering ease of control of production parameters, versatile pore geometry, 100% pore connectivity, and repeatability.

In the patent document showing the state of the art with the number of 2018/11205 and with the title "Osteogenic osteoconductive biocompatible composite nanofiber scaffold for bone and cartilage tissue damage repair" it is stated that it is made of Polycaprolactone (PCL), bovine gelatin (GE) and Bovine Hydroxyapatite (BHA) to be used in bone and cartilage tissue damage repair applications as a biocompatible, osteogenic, osteoconductive biomimetic composite nanofiber scaffold produced with the electrospinning method and which are selected because of their high biocompatibility, chemical properties, and similarity to bone, with non-toxic solvent system of these materials, and the parameters of the composite nanofiber production process by electrospinning method are described along with the physical, morphological, chemical, mechanical, and biological properties of PCL/GE/BHA nanofibers, and with the statistical significance of cell proliferation and viability test results, composite nanofiber scaffolds produced by osteoblast biocompatible with human cells.

In the patent with the document number of 2019/12510 and with the title "A composite biomaterial suitable to be used in bone tissue repair", which shows the state of the art, including the steps of boron and polylactic acid-containing composite biomaterials suitable for use in bone tissue repair and their production, weighing and melting the polylactic acid powder, adding and mixing boron powder into molten polylactic acid, cooling the polylactic acid and boron mixture to become pellets, producing polylactic acid and boron-containing filaments by extruding the pellets, and producing composite biomaterials by processing the filaments.

In the patent document with the number of 2016/18844 and with the title "Silver-ion added calcium phosphate-based bioceramic artificial bone tissue with antimicrobial properties", which shows the state of the art, an artificial bone tissue material, which can be used for the treatment of osteomyelitis and implant-related bone infections in humans and animals is produced the most important feature of which is also to treat bone infections which result in cavities, as a biocompatible artificial bone tissue material with anti-microbial properties obtained by applying nano-technological approaches, with the basic structure of calcium phosphate with silver ion added with the Wet Chemical Method used in the production of silver-added antimicrobial bioceramics, the powders are Biphasic (HAP+TCP) and Triphasic (HAP+TCP+Bioglass), silver ions are added to the structure, giving antimicrobial properties, the synthesized nanopowder and the material that will form the porous structure mixed in the desired amounts as an artificial bone tissue material.

SUMMARY

With our invention, the purpose is to increase the transmission rate of the growth factors of the 3D polymer and β-Tricalcium Phosphate (β-TCP) scaffold structure formed here.

Another purpose of the invention was to obtain a hybrid artificial bone tissue implant absorbing mechanical vibrations, which can be used with titanium structures supporting autologous regeneration, allowing the saturation of bone marrow, blood, and nutrients with an architectural structure imitating trabecular bone.

Another purpose of the invention was to obtain a 3D and porous design to support cell adhesion, penetration, proliferation, and extracellular matrix (ECM (Extracellular Matrix)) deposition.

Another purpose of the invention was to reinforce bone tissues that cannot be shaped or volumized again.

Another purpose of the invention was to increase the growth factors by providing cell adhesion with HA coating with scaffold production and 3D printing technique.

BRIEF DESCRIPTION OF THE DRAWINGS

In the drawings on the biological tissue implant, which is the subject of the invention.

Figure 1:
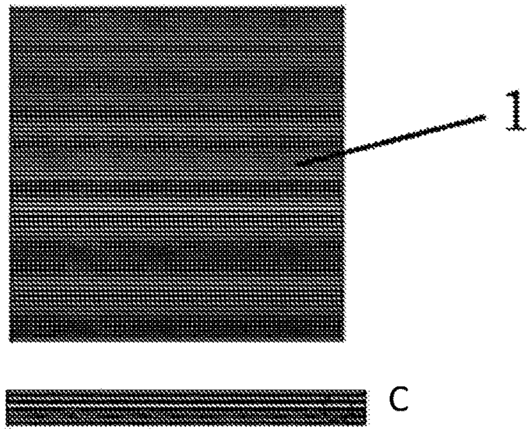
FIG. 1: The schematic view of the cylindrical tissue scaffold.
Figure 2:
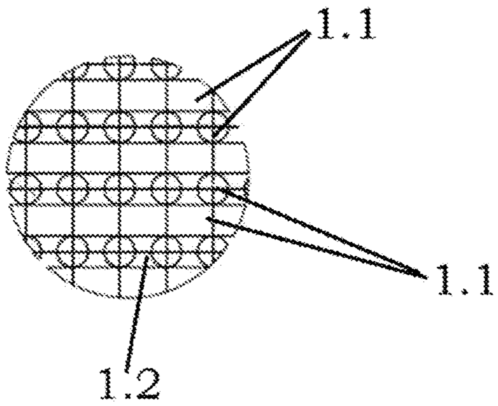
FIG. 2: Detail view of the cylindrical tissue scaffold.
Figure 3:
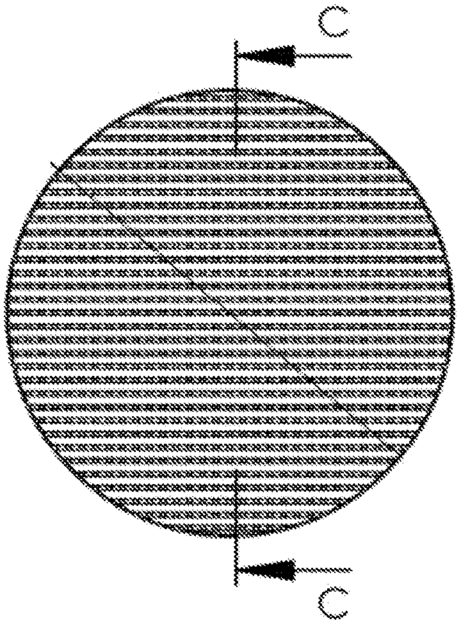
FIG. 3: The schematic view of the front face of the cylindrical scaffold.
Figure 4:
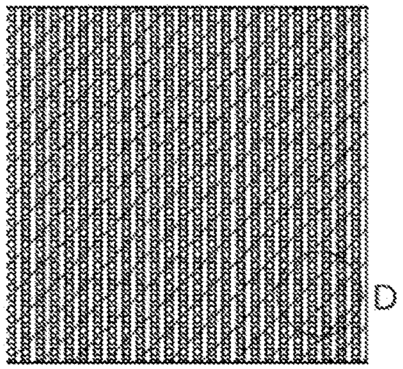
FIG. 4: The schematic view of the cartilage repair patch.
Figure 5:
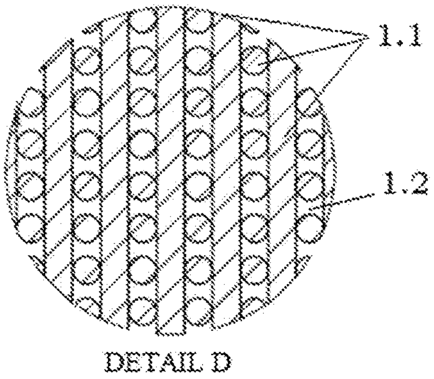
FIG. 5: The schematic and detailed view of the filament structure.
Figure 6:
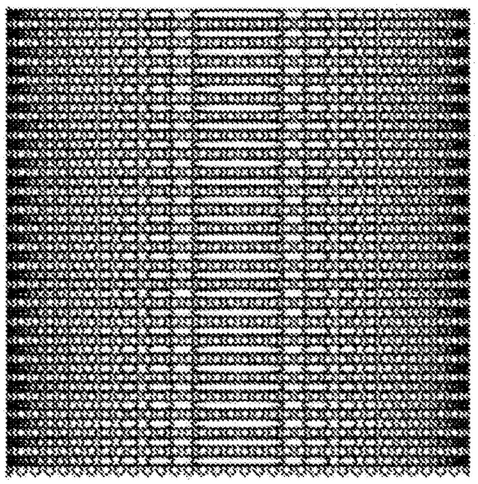
FIG. 6: The schematic view of the filament array (cross).
Figure 7:
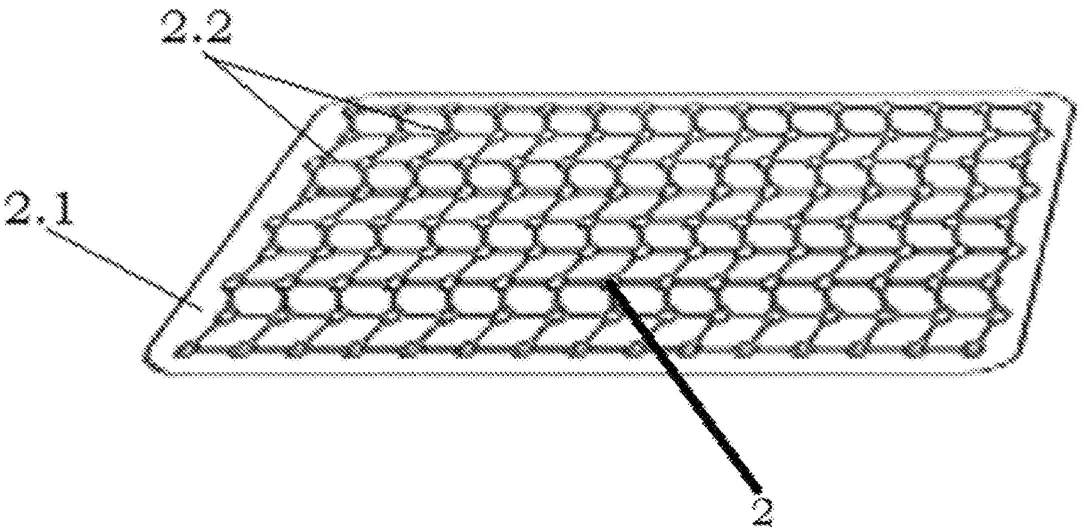
FIG. 7: The schematic-perspective view of the hybrid system.

The parts in the figures are numbered one by one and are given below:

- 1. Tissue scaffold
  - 1.1. Filaments
  - 1.2. Chamber
- 2. Hybrid implant
  - 2.1. Polymer layer
  - 2.2. Titanium mesh

DETAILED DESCRIPTION OF THE EMBODIMENTS

Our invention is basically the creation of a 3D polymer and β-Tricalcium Phosphate (β-TCP) scaffold structure (tissue scaffold) and a biological tissue implant allowing/supporting cell infiltration by using the added manufacturing process, coating it with physiological-buffered HA solution with the deep coting method to increase the delivery rate of growth factors and enlarge their areas allowing the use of titanium mesh plate or contoured structures.

Since a normal hyaluronic acid molecule is metabolized and excreted 12 hours after it is injected into the human skin, cross-links are used in HA molecules to make it permanent. The cross-linking of hyaluronic acid makes the solution more viscous increasing its effect by prolonging the residence time in the implant.

The layers are connected at angles to support extracellular matrix (ECM) interaction in our invention, and the overlapping structures are overlapped obliquely. The resulting structures have an hfa 50-70-micron porous structure and support the formation of vascularized tissue with osteoconductive effect.

The 3D tissue scaffold formed as a result of extrusion crates micro-cracks on the body with the cryo-shocking method, and the deep encapsulation of hyaluronic acid into the body is increased. The HA solution is 20-70 μm-1 mL per square centimeter of scaffold body.

It is a biological tissue implant and its features are;

Overlapping filament layers (1.1) connected at angles to support Extracellular Matrix (ECM) interaction with each other connected by angling at 90° to each other, Oblige overlapping structures of the third filament layer, Supporting the formation of vascularized tissue with the osteoconductive effects of 50-70-micron pore structure of the obtained structures, Increasing the encapsulation of the hyaluronic acid deep into the body by creating micro cracks with the cryo-shock method or vacuum drying system of the 3D tissue scaffold (1) formed as a result of extrusion, Attachment and coating of empass or hot polymer (2.1) onto the surface of the titanium mesh (2.2) by extrusion, Bone augmentation (to patients with a bone deficiency) to repair severely traumatic and degraded tissues is not suitable for reshaping especially in the jaw region if the discomfort has gained aesthetic concern. It will be an important solution for bone tissue that cannot be reshaped or volumized.

Another feature of the system is the polymer implant technology that has a hybrid structure.

Bionic titanium, which is the raw material of the scaffold obtained, is coated on the mesh plate with the extrusion or drying method. The vascularized tissue is re-grown and formed inward by reshaping the volumetric defect. The tissue is protected against environmental loads while shaped with a titanium mesh scaffold thanks to this technology. The reinforced titanium plates provide a barrier by minimizing softness. The titanium mesh also provides radiographic visibility. It is of vital importance especially for the defects in the head region with its high ability to imitate bone.

A device and method for providing surgical therapy for the in situ treatment and repair of intra-articular cartilage lesions and/or defects are described with this invention.

The device is an implantable, biocompatible, and physiologically absorbable laminate cartilage repair patch. The cartilage repair patch is adapted to be placed near a first outer cell occlusive layer, a subchondral bone wound site.

The hybrid structure (2) fully supports bone augmentation, acts as a barrier, has high-density polymer tissue, helps in the regeneration, provides potential fibrovascular growth, covers the polymer structure (2.1) on titanium mesh (2.2), and provides form and volume to the tissue, which has lost its volumetric integrity, and has the feature allowing the tissue to grow inward. The thin polymer layer (2.1) on the implants minimizes the upper surface tissue adhesion supporting vascular tissue growth by increasing the lower surface porous structure.

A second outer cell has a permeable HA layer and a cartilagenic matrix (architecture) between the first and second layers. The cartilagenic matrix and the permeate layer surface area have the characteristics of a receiving point for the diffusion of autologous stem cells and has components supporting the production of hyaline-like cartilage in the presence of autologous stem cells.

The accurate combination of nano-enhancer and hydrogel polymer, hyaluronic acid coating method to produce mechanically firm, electrically conductive, bioactive;

It contains the following process steps;

The preparation of solutions with a magnetic stirrer at room temperature with 10 mg/ml sodium hyaluronate (1 million Da, medical-grade) in physiological buffer (PBS pH 7.4), Completing the work by coating the scaffolds with dip-coating method into the solution and drying at vacuum oven at 50° C. for 3 days, The biological tissue implant can be manufactured in cylindrical, square, and free forms anatomical shapes allowing rapid implantation requiring minimal manipulation. The tissue implant, which is suitable for specific shapes, can be produced in multiple thicknesses and models that are specific to anatomical regions to meet clinical needs, and the reinforced layer increases strength and contours. The fixation hole/position allows optimum screw placement, anatomical shape, and the radial titanium mesh design minimize the cutting option offering many fixation options and promoting cell preinflation by gaining micro-mobility.

If desired, therapeutic concentration, stem cell, or growth factor can be integrated into the scaffold structure.

β-Tricalcium Phosphate (β-TCP) is included in the prepared PCL granule by 3-15%. In this way, the toughness values of the scaffold body formed by reducing the viscosity of the polymer are increased.

β-Tricalcium Phosphate (β-TCP) is a biocompatible, radiopaque, and resorbable osteoconductive material as an important factor supporting the formation of new bone in the defect area.

What is claimed is:

1. A method of obtaining a biological tissue implant, comprising: forming, by an additive manufacturing process comprising extrusion deposition, a three-dimensional scaffold structure comprising a polymer and β-tricalcium phosphate (β-TCP), the scaffold structure allowing/supporting cell infiltration and comprising polymer filaments arranged in overlapping filament layers; connecting the filament layers to each other at angles, including connecting a first filament layer and a second filament layer by angling at 90 degrees with each other, to support extracellular matrix (ECM) interaction; overlapping a third filament layer obliquely relative to at least one of the first filament layer and the second filament layer; providing the scaffold structure with a 50-70-micron pore structure supporting the formation of vascularized tissue with osteoconductive effect; coating the scaffold structure by dip-coating the scaffold structure in a physiological buffer solution comprising hyaluronic acid (HA) and drying the scaffold structure; forming microcracks in a scaffold body by a cryo-shock method or a vacuum drying system to increase encapsulation of the hyaluronic acid within the scaffold body; and attaching and coating a polymer layer onto a surface of a titanium mesh plate by extrusion, thereby obtaining the biological tissue implant configured for use with the titanium mesh plate or a contoured structure.

2. The method according to claim 1, wherein dip-coating and drying the scaffold structure comprises: preparing, with a magnetic stirrer at room temperature, a solution comprising 10 mg/ml sodium hyaluronate (1 million Da, medical-grade) in a physiological buffer comprising phosphate buffered saline (PBS) at pH 7.4; dip-coating the scaffold structure in the solution; and drying the scaffold structure for 3 days at 50° C. in a vacuum oven.

3. The method according to claim 1, wherein cross-links are used in the hyaluronic acid (HA) molecules to make the hyaluronic acid permanent in the biological tissue implant.

4. The method according to claim 1, wherein forming microcracks comprises forming microcracks in the scaffold body with the cryo-shock method in the three-dimensional tissue scaffold formed by extrusion deposition.

5. The method according to claim 1, wherein the biological tissue implant comprises an implantable, biocompatible, and physiologically absorbable laminate cartilage repair patch adapted to be placed near a subchondral bone wound site on a first outer cell occlusive layer.

6. The method according to claim 1, wherein the biological tissue implant comprises a first outer cell occlusive layer and a second outer cell having a permeable hyaluronic acid (HA) layer, and a cartilagenic matrix disposed between the first outer cell occlusive layer and the second outer cell.

7. The method according to claim 6, wherein the cartilagenic matrix and a surface area of the permeable hyaluronic acid (HA) layer have characteristics of a receiving point for the diffusion of autologous stem cells, and have components supporting the production of cartilage in the presence of autologous stem cells.

8. The method according to claim 1, wherein the biological tissue implant comprises a hybrid structure comprising a polymer layer on a titanium mesh, the hybrid structure fully supporting bone augmentation, acting as a barrier, having high-density polymer tissue, helping regeneration, providing potential fibrovascular growth, providing form and volume to tissue which has lost its volumetric integrity, and allowing the tissue to grow inward.

9. The method according to claim 1, wherein the biological tissue implant is manufactured in cylindrical, square, or free-form anatomical shapes.

10. The method according to claim 1, further comprising integrating at least one of a stem cell and a growth factor into the scaffold structure at a therapeutic concentration.

11. The method according to claim 1, wherein β-tricalcium phosphate (β-TCP) is included in a prepared polycaprolactone (PCL) granule by 3-15%, the β-tricalcium phosphate (β-TCP) being a biocompatible, radiopaque, and resorbable osteoconductive material supporting new bone formation in a defect area.

12. The method according to claim 2, wherein cross-links are used in the hyaluronic acid (HA) molecules to make the hyaluronic acid permanent in the biological tissue implant.

13. The method according to claim 2, further comprising forming microcracks in the scaffold body with a cryo-shock method in the three-dimensional tissue scaffold formed by extrusion deposition.

14. The method according to claim 3, further comprising forming microcracks in the scaffold body with a cryo-shock method in the three-dimensional tissue scaffold formed by extrusion deposition.

15. The method according to claim 2, wherein the biological tissue implant comprises an implantable, biocompatible, and physiologically absorbable laminate cartilage repair patch adapted to be placed near a subchondral bone wound site on a first outer cell occlusive layer.

16. The method according to claim 3, wherein the biological tissue implant comprises an implantable, biocompatible, and physiologically absorbable laminate cartilage repair patch adapted to be placed near a subchondral bone wound site on a first outer cell occlusive layer.

17. The method according to claim 4, wherein the biological tissue implant comprises an implantable, biocompatible, and physiologically absorbable laminate cartilage repair patch adapted to be placed near a subchondral bone wound site on a first outer cell occlusive layer.

18. The method according to claim 2, wherein the biological tissue implant comprises a first outer cell occlusive layer and a second outer cell having a permeable hyaluronic acid (HA) layer, and a cartilagenic matrix disposed between the first outer cell occlusive layer and the second outer cell.

19. The method according to claim 3, wherein the biological tissue implant comprises a first outer cell occlusive layer and a second outer cell having a permeable hyaluronic acid (HA) layer, and a cartilagenic matrix disposed between the first outer cell occlusive layer and the second outer cell.

20. The method according to claim 4, wherein the biological tissue implant comprises a first outer cell occlusive layer and a second outer cell having a permeable hyaluronic acid (HA) layer, and a cartilagenic matrix disposed between the first outer cell occlusive layer and the second outer cell.

* * * * *